(12) United States Patent
Schmieding et al.

(10) Patent No.: US 8,939,980 B2
(45) Date of Patent: Jan. 27, 2015

(54) SYSTEM FOR ACL RECONSTRUCTION USING RETROGRADE CUTTER

(71) Applicant: Arthrex, Inc., Naples, FL (US)

(72) Inventors: Reinhold Schmieding, Naples, FL (US); Jeffrey Wyman, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/203,171

(22) Filed: Mar. 10, 2014

(65) Prior Publication Data

US 2014/0194880 A1 Jul. 10, 2014

Related U.S. Application Data

(62) Division of application No. 11/598,093, filed on Nov. 13, 2006, now Pat. No. 8,668,738.

(60) Provisional application No. 60/794,512, filed on Apr. 25, 2006, provisional application No. 60/735,197, filed on Nov. 10, 2005.

(51) Int. Cl.
*A61B 17/00* (2006.01)
*A61B 17/04* (2006.01)
*A61B 17/16* (2006.01)
(Continued)

(52) U.S. Cl.
CPC ....... *A61B 17/00234* (2013.01); *A61B 17/0401* (2013.01); *A61B 17/1617* (2013.01); *A61B 17/1675* (2013.01); *A61B 17/1714* (2013.01); *A61B 17/1764* (2013.01); *A61B 17/32002* (2013.01); *A61B 17/0485* (2013.01); *A61B 2017/0404* (2013.01); *A61B 2017/320032* (2013.01); *A61B 2019/462* (2013.01)

USPC .............................................. 606/80; 606/96

(58) Field of Classification Search
CPC .. A61B 17/16; A61B 17/1614; A61B 17/164; A61B 17/1675; A61B 17/1714
USPC ................................ 606/79–88, 96–98, 232; 623/13.11–13.2
See application file for complete search history.

(56) References Cited

U.S. PATENT DOCUMENTS

| | | |
|---|---|---|
| 4,034,418 A | 7/1977 | Jackson et al. |
| 5,211,647 A | 5/1993 | Schmieding |

(Continued)

OTHER PUBLICATIONS

Y. Ohkoshi, et al., "Description of a New Endoscopic Posterior Cruciate Ligament Reconstruction and Comparison with a 2-Incision Technique", Arthroscopy: The Journal of Arthroscopic and Related Surgery, vol. 19, No. 8, Oct. 2003, pp. 825-832.

(Continued)

*Primary Examiner* — Matthew Lawson
(74) *Attorney, Agent, or Firm* — Dickstein Shapiro LLP

(57) ABSTRACT

A system for anterior cruciate ligament (ACL) reconstruction using holes in bone created by retrograde cutting. A rotary cutter, mounted onto an insertion post of a tibial guide, is inserted through an anteromedial portal and the rotary cutter placed on the anatomical origin of an ACL tibial insertion. A drill pin is drilled through the tibia and advanced until it contacts and engages a cannulation in the rotary cutter on the guide. Further rotation of the drill pin disengages the rotary cutter from the guide. The retrograde drill pin is then retracted and simultaneously rotated for retrograde cutting of a socket or tunnel of desired depth in the tibia. A similar system is provided to form a socket or tunnel in the femur except that a femur guide is used in place of the tibial guide.

5 Claims, 23 Drawing Sheets

(51) Int. Cl.
*A61B 17/17* (2006.01)
*A61B 17/32* (2006.01)
*A61B 19/00* (2006.01)

(56) References Cited

U.S. PATENT DOCUMENTS

| | | |
|---|---|---|
| 5,374,270 A | 12/1994 | McGuire et al. |
| 5,549,613 A * | 8/1996 | Goble et al. ............... 606/80 |
| 5,713,905 A | 2/1998 | Goble et al. |
| 5,919,196 A | 7/1999 | Bobic et al. |
| 6,015,411 A * | 1/2000 | Ohkoshi et al. ............ 606/80 |
| 6,120,511 A * | 9/2000 | Chan ........................... 606/96 |
| 6,132,433 A | 10/2000 | Whelan |
| 6,149,654 A | 11/2000 | Johnson |
| 6,280,474 B1 | 8/2001 | Cassidy et al. |
| 6,783,533 B2 | 8/2004 | Green et al. |
| 6,958,067 B2 | 10/2005 | Whittaker et al. |
| 7,160,305 B2 | 1/2007 | Schmieding |
| 7,238,189 B2 | 7/2007 | Schmieding et al. |
| 7,569,059 B2 | 8/2009 | Cerundolo |
| 2002/0156484 A1 | 10/2002 | McKernan et al. |
| 2004/0176771 A1 | 9/2004 | Schmieding |
| 2004/0199166 A1 * | 10/2004 | Schmieding et al. .......... 606/79 |
| 2006/0129162 A1 | 6/2006 | McKernan et al. |
| 2006/0149283 A1 | 7/2006 | May et al. |
| 2006/0271059 A1 | 11/2006 | Reay-Young et al. |
| 2006/0293689 A1 | 12/2006 | Miller et al. |

OTHER PUBLICATIONS

Y. Ohkoshi, et al., "A New Endoscopic Posterior Cruciate Ligament Reconstruction: Minimization of Graft Angulation", Arthroscopy: The Journal of Arthroscopic and Related Surgery, vol. 17, No. 3, Mar. 2001, pp. 258-263.

* cited by examiner

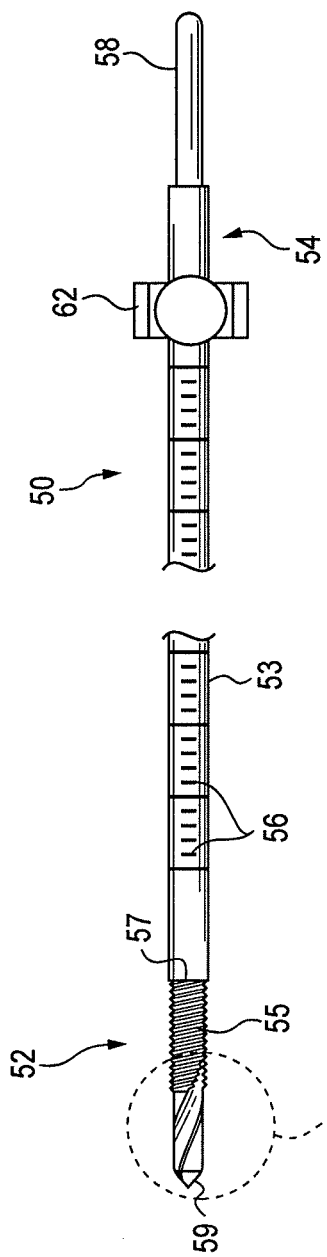
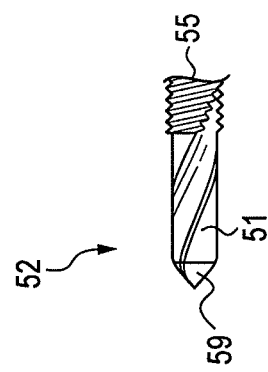
FIG. 2A
FIG. 2B

SYSTEM FOR ACL RECONSTRUCTION USING RETROGRADE CUTTER

This is a divisional of U.S. application Ser. No. 11/598,093, filed Nov. 13, 2006, now U.S. Pat. No. 8,668,738, which claims the benefit of U.S. Provisional Application No. 60/735,197, filed Nov. 10, 2005 and U.S. Provisional Application No. 60/794,512, filed Apr. 25, 2006.

BACKGROUND OF THE INVENTION

1. Field of the Invention

The present invention relates to the field of surgery and, more particularly, to methods of reconstructive knee surgery.

2. Description of the Related Art

Methods of anterior cruciate ligament (ACL) reconstruction using interference screw fixation are described, for example, in U.S. Pat. Nos. 5,211,647 and 5,320,626. In general, these methods of ACL reconstruction involve drilling a tunnel through the tibia, drilling a closed tunnel (socket) into the femur, inserting a substitute ACL graft into the tunnels, and securing the grafts to the walls of the tibial and femoral tunnels using interference screws or the like. Accurate positioning of the tibial and femoral tunnels is accomplished using a drill guide, examples of which are disclosed in U.S. Pat. Nos. 5,269,786 and 5,350,383, incorporated herein by reference.

One drawback of the described methods of ACL reconstruction is that forming the tibial tunnel involves removal of significant amounts of bone material. U.S. Pat. No. 5,603,716 discloses a technique for ACL reconstruction that avoids the above-noted problem by forming sockets in both the femur and the tibia using a coring bone harvester. The harvester is impacted into bone to a desired depth so that bone material collects as a bone core within the harvester tube. The bone core is extracted from the bone socket using a simultaneous twisting and pulling motion. Such harvesting of bone cores in the joint is technically difficult. Accordingly, the need exists for a method of ACL reconstruction, and related instrumentation, that provides tibial socket formation without the need for extracting a bone core to form a bone socket and to avoid drilling through growth plates in skeletally immature patients. There is also a need for a minimally invasive method of ACL reconstruction, and related instrumentation, that provides drilling of femoral and tibial sockets or tunnels independently of one another and minimizes incisions of distal cortices and reduces intraarticular bone fragmentation of tunnel rims.

SUMMARY OF THE INVENTION

The present invention overcomes the disadvantages of the prior art and fulfills the needs noted above by providing techniques and apparatus for creating bone sockets and/or tunnels by drilling in a retrograde manner. The present invention advantageously utilizes a preloaded retrograde rotary cutter that provides exact visual replication of tunnel or socket diameter prior to drilling both the tibial and femoral sockets and/or tunnels.

More specifically, the present invention provides a method for ACL reconstruction which includes the steps of introducing a guide having a rotary cutter engaged on a distal end thereof into a joint through a portal, introducing a pin having a distal end into the joint, inserting the distal end of the pin into a corresponding cannulation in the rotary cutter, engaging the rotary cutter with the distal end of the pin and simultaneously disengaging the rotary cutter from the guide by rotating the pin, and drilling into the bone to create the socket by rotating the rotary cutter and moving the rotary cutter in a retrograde manner using the pin.

The present invention also includes a system for carrying out the above method, including a rotary cutter comprising a cylindrically shaped body provided with a threaded cannulation and radially outward cutting teeth for retrograde drilling of a socket in bone, a guide comprising a threaded post for engaging and mounting the rotary cutter, and a drill pin having a distal end corresponding to the cannulation of the rotary cutter, for engaging the rotary cutter. The system is designed so that the rotary cutter is transferred from the guide to the drill pin by advancing the drill pin into the cannulation of the rotary cutter and rotating the drill pin in a first direction to engage the drill pin with the rotary cutter mounted on the guide, and simultaneously disengage the rotary cutter from the guide.

The method and system for ACL reconstruction of the present invention may be employed in posterior cruciate ligament (PCL) reconstruction as well.

Other features and advantages of the present invention will become apparent from the following description of the invention which refers to the accompanying drawings.

BRIEF DESCRIPTION OF THE DRAWINGS

FIGS. 2A and 2B illustrate a retrograde pin according to the present invention;

DETAILED DESCRIPTION OF THE PREFERRED EMBODIMENTS

The present invention provides a technique for forming femoral and tibial bone sockets in a retrograde manner during ligament reconstruction, for example, anterior cruciate ligament (ACL) reconstruction. The present invention also provides a method of graft insertion and fixation employed in connection with the femoral and tibial sockets formed in accordance with the present invention.

Figure 1C:
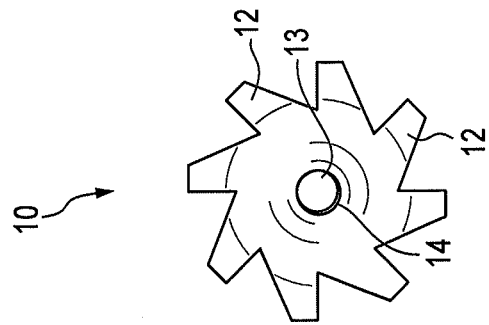
FIGS. 1A-1C illustrate a retrograde rotary cutter according to the present invention.
Figure 1B:
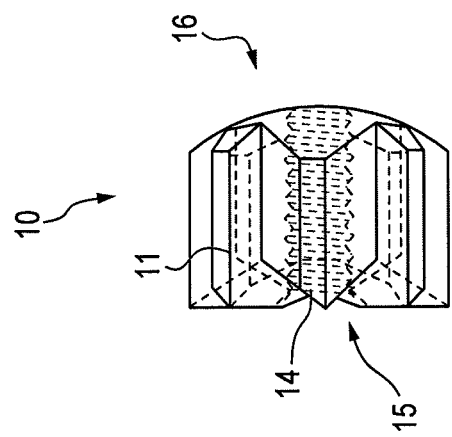
Figure 1A:
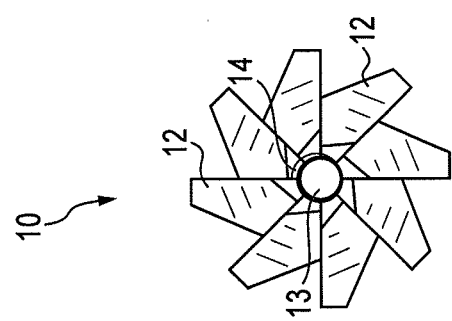

Referring now to the drawings, where like elements are designated by like reference numerals, FIGS. 1-2 illustrate a retrograde rotary cutter 10 (FIGS. 1A-1C) which is adapted to be threadingly engaged with a cannulated retrograde drill pin 50 (FIGS. 2A-2C).

Referring to FIGS. 1A-1C, the retrograde rotary cutter 10 features a cylindrical body 11 having a plurality of cutting teeth 12 radiating symmetrically. A cannulation 13 through body 11 is provided with internal screw threads 14. Cutting teeth 12 have edges extending radially from cannulation 13 on a proximal cutting face 15, seen in plan view in FIG. 1A. The edges of cutting teeth 12 continue axially along the side of the retrograde rotary cutter 10, which is oriented orthogonally to proximal cutting face 15. The edges end at a smooth, rounded distal end 16 of retrograde rotary cutter 10. Retrograde rotary cutter 10 is provided in a selected diameter corresponding to graft size of diameter substantially equal to the diameter of a replacement graft substitute for an anterior cruciate ligament (ACL).

Referring to FIGS. 2A-2B, retrograde drill pin 50 features a fluted region 51 formed on distal end 52 of cannulated body 53, as shown in detail in FIG. 2B. Cannulated body 53 has a proximal end 54. The cannulated body 53 is provided with screw threads 55 at distal end 52. The screw threads 55 are fashioned to engage corresponding threads 14 of retrograde rotary cutter 10. Accordingly, the outer diameter of threaded region 55 closely approximates the diameter of cannula 13 of the retrograde rotary cutter 10, to allow secure engagement of the outer threaded region 55 with the inner threads 14 of retrograde rotary cutter 10.

Retrograde drill pin 50 features visible calibrated depth markings 56 lased onto the cannulated body 53. Between threads 55 and depth markings 56, a shoulder 57 is formed to provide a stop where threads 55 end. The lumen of cannulated body 53 accepts a trocar 58 having a pointed tip 59. When the trocar is removed, a strand can be passed through the lumen of the cannulated body 53, as described below in greater detail. The proximal end 54 of cannulated body 53 is configured for chucking into a rotary driver (not shown). The distal end 52 of cannulated body 53 is open at the tip to expose the pointed end 59 when the trocar 58 is inserted into the cannulated body 53, as when drilling the assembled retrograde drill pin 50 into bone. Retrograde drill pin 50 includes a setscrew collar 62 for securing the trocar 58 in the cannulated body 53.

Figure 3A:
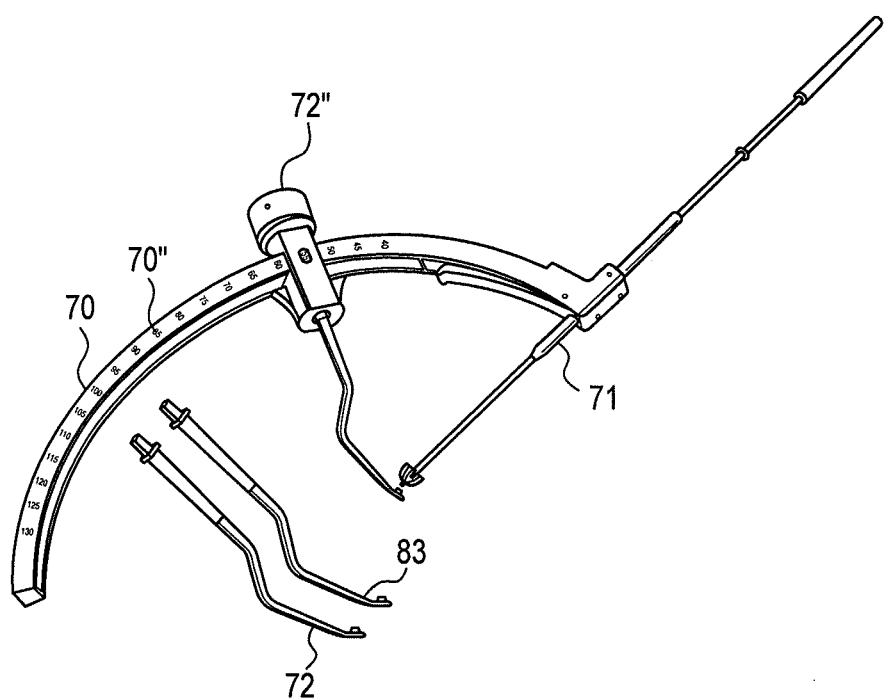
FIGS. 3A and 3B illustrate a C-ring and a retrograde rotary cutter according to the present invention.
Figure 3B:
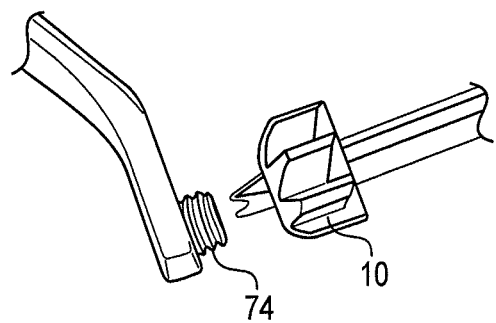

Referring to FIGS. 3A-3B, C-ring 70 features visible calibrated angular markings 70" circumferentially lased onto the body (not shown). A groove (not shown) near one end of the C-ring 70 is provided to secure a retrograde drill guide sleeve 71. A holding member 72" movable along the circumference of C-ring 70 is provided to secure a tibial guide 72 or a femoral guide 83. The holding member 72" facilitates angular adjustment of the tibial guide 72 or the femoral guide 83 relative to the retrograde drill guide sleeve 71. The tibial guide 72 or the femoral guide 83 is provided with an insertion post 74 to allow secure engagement of the retrograde rotary cutter 10. A fixed angle drill guide may be used instead of the drill guide C-ring 70.

A method of using the C-ring 70, the retrograde drill pin 50, the tibial guide 72, and the retrograde rotary cutter 10 to create a tibial socket 81 of the present invention is described below with reference to FIGS. 4-12, which illustrate a schematic anterior view of a knee in which ACL reconstruction is performed according to the present invention. In the following embodiment of the present invention, a tibial socket 81 (shown completed in FIGS. 10-12) is formed in a tibia 75.

Figure 4:
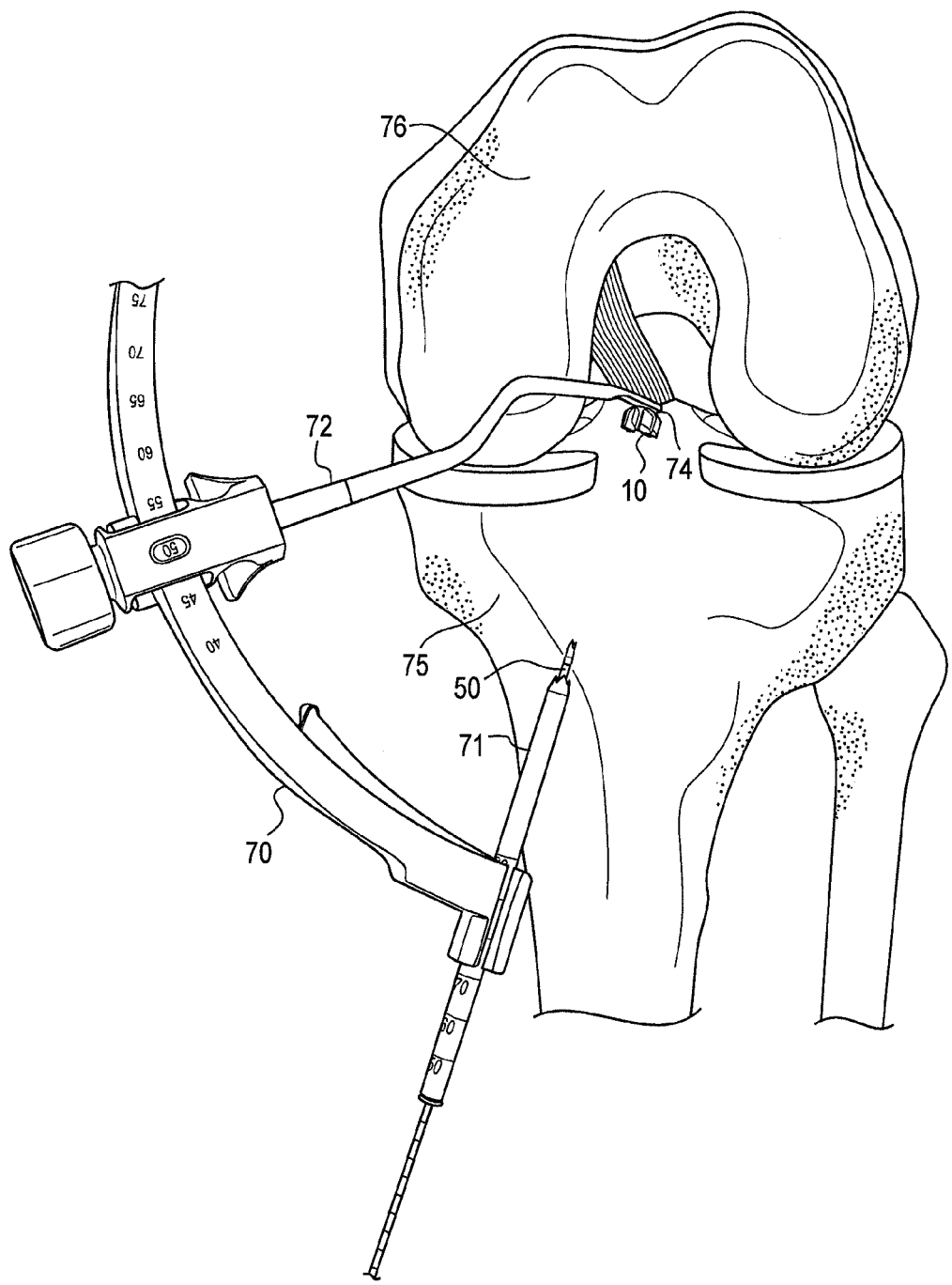
FIG. 4 schematically illustrates an initial stage in the formation of a tibial socket according to the present invention.
Figure 5:
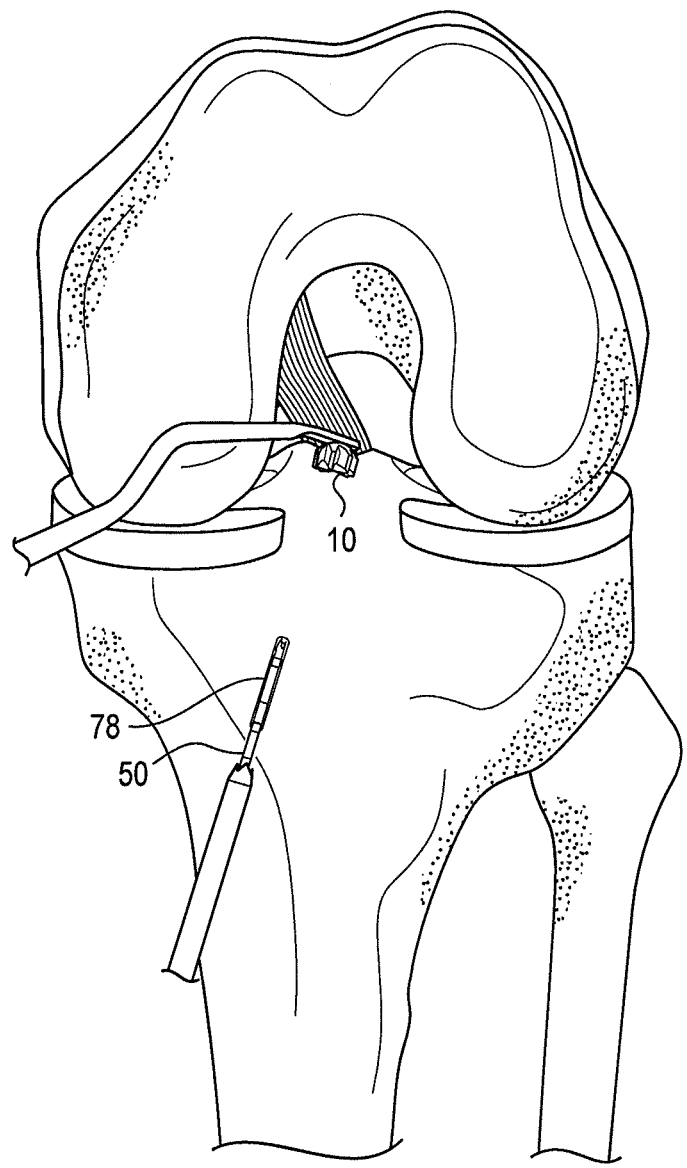
FIG. 5 schematically illustrates the formation of a tibial socket at a stage subsequent to that shown in FIG. 4.

Referring to FIGS. 4-5, the appropriate diameter retrograde rotary cutter 10 is threaded onto the insertion post 74 of the tibial guide 72. The tibial guide 72 is inserted through the anteromedial portal (not shown) and the retrograde rotary cutter 10 is placed on the anatomical origin of the ACL tibial insertion. The retrograde drill pin 50 is adjusted to an appropriate angle, to avoid existing tunnels and fixation hardware, for insertion onto the tibia 75.

Once the anatomical position in the joint for the tibial socket has been identified, and the appropriate drilling angle has been selected on C-ring 70, the retrograde drill guide sleeve 71 is inserted into the tibia 75 through a small stab incision on the tibia 75. The retrograde drill pin 50 is drilled through the tibia, in a forward direction, to create pin hole 78 of a given diameter, for example 3 mm, as shown in FIG. 5.

Figure 6:
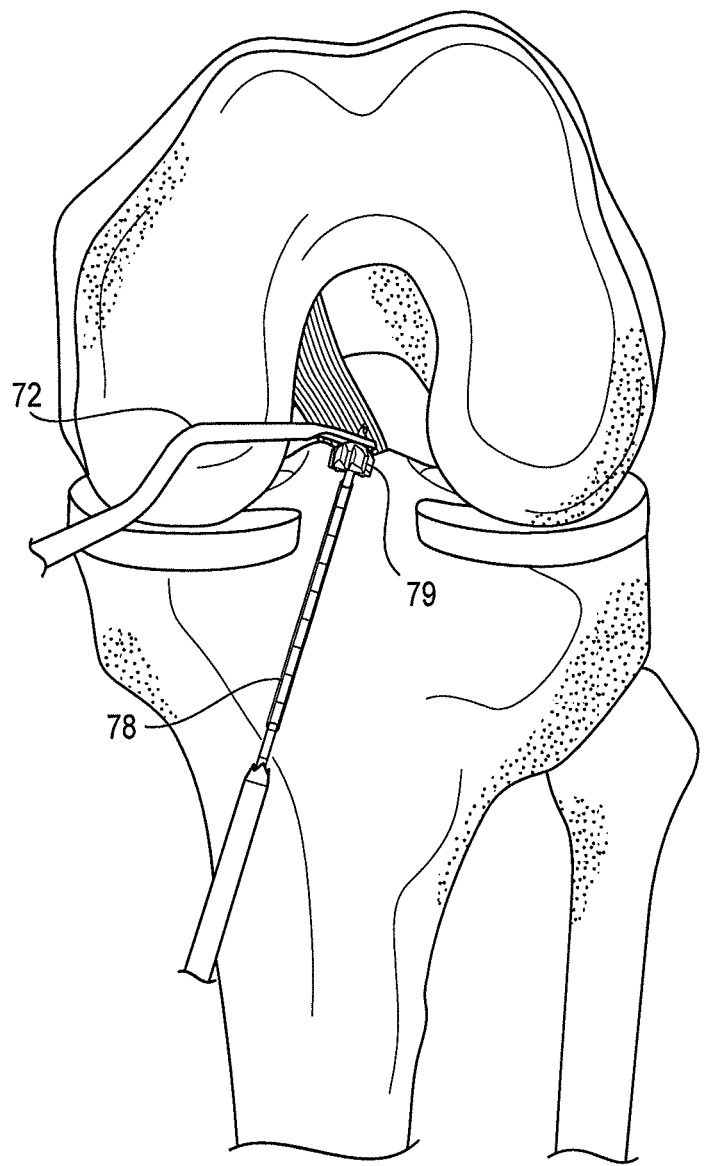
FIG. 6 schematically illustrates the formation of a tibial socket at a stage subsequent to that shown in FIG. 5.
Figure 7:
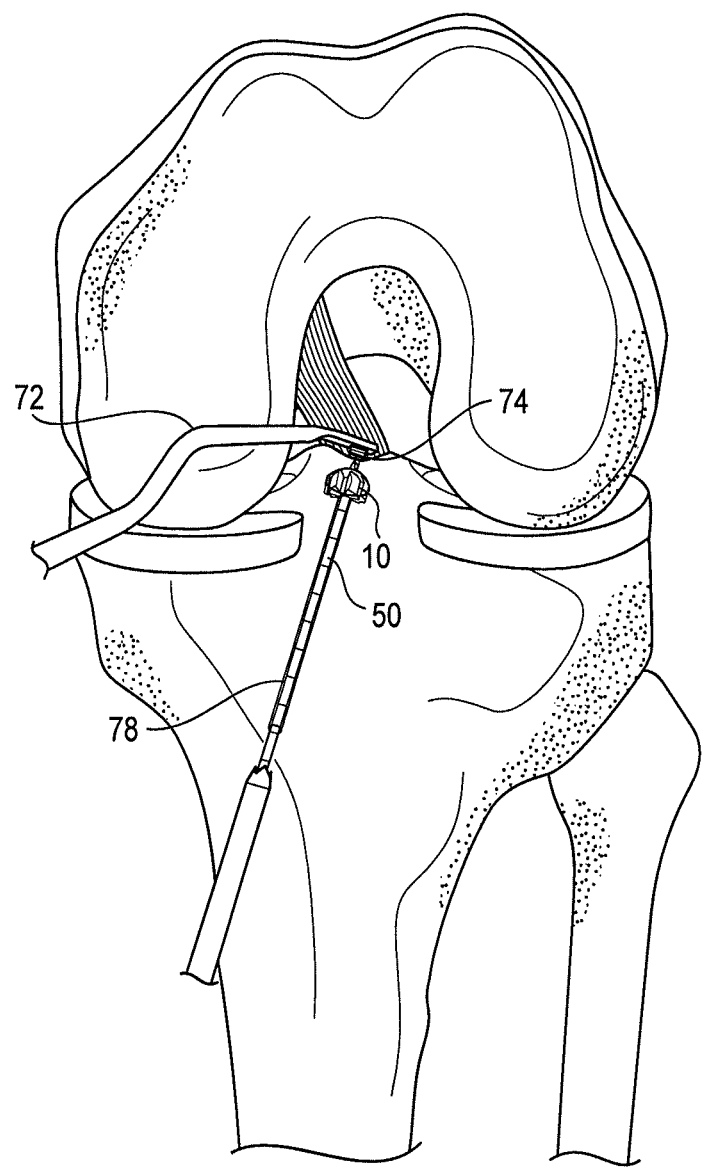
FIG. 7 schematically illustrates the formation of a tibial socket at a stage subsequent to that shown in FIG. 6.

The retrograde drill pin 50 is drilled through the tibia 75 until contact is made with the retrograde rotary cutter 10 under arthroscopic control, as shown in FIG. 6. Referring to FIG. 7, as threads of the retrograde drill pin 50 engage the retrograde rotary cutter 10, the reverse threads on the insertion post 74 of the tibial guide 72 facilitate simultaneous disengagement of the retrograde rotary cutter 10 from the insertion post 74 onto the retrograde drill pin 50. Once securely engaged within the retrograde rotary cutter 10, the retrograde drill pin 50 is rotated with a power driver (not shown) and retracted (retrograde) to cut through the tibial joint surface. In another embodiment, the attachment of the retrograde rotary cutter 10 to the retrograde drill pin 50 may be accomplished using a snap-fit.

Figure 8A:
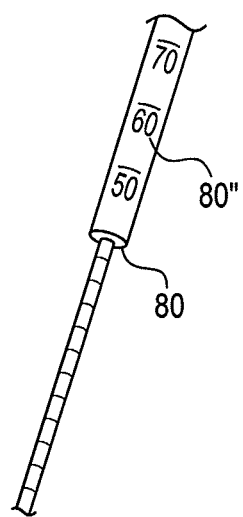
FIGS. 8A and 8B illustrate a drill depth grommet on a retrograde drill pin according to the present invention.
Figure 8B:
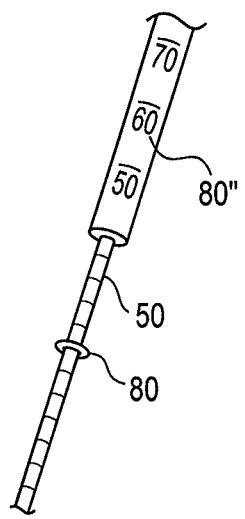
Figure 9A:
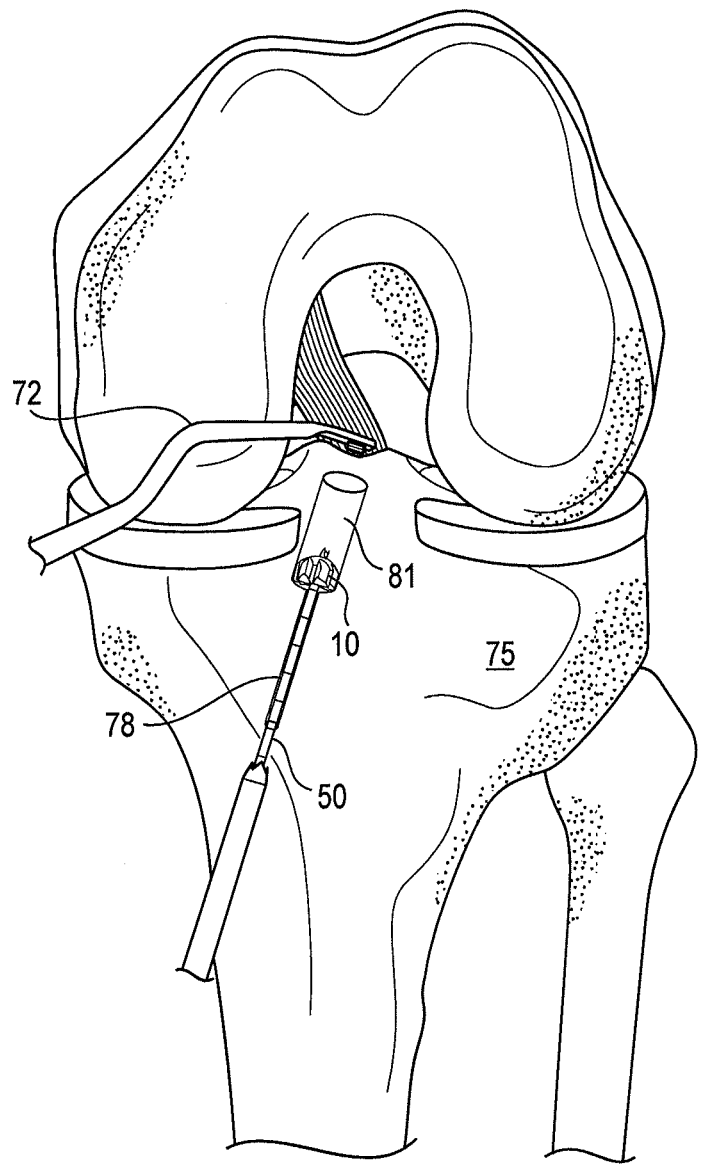
FIGS. 9A and 9B schematically illustrates the formation of a tibial socket at a stage subsequent to that shown in FIG. 7.
Figure 9B:
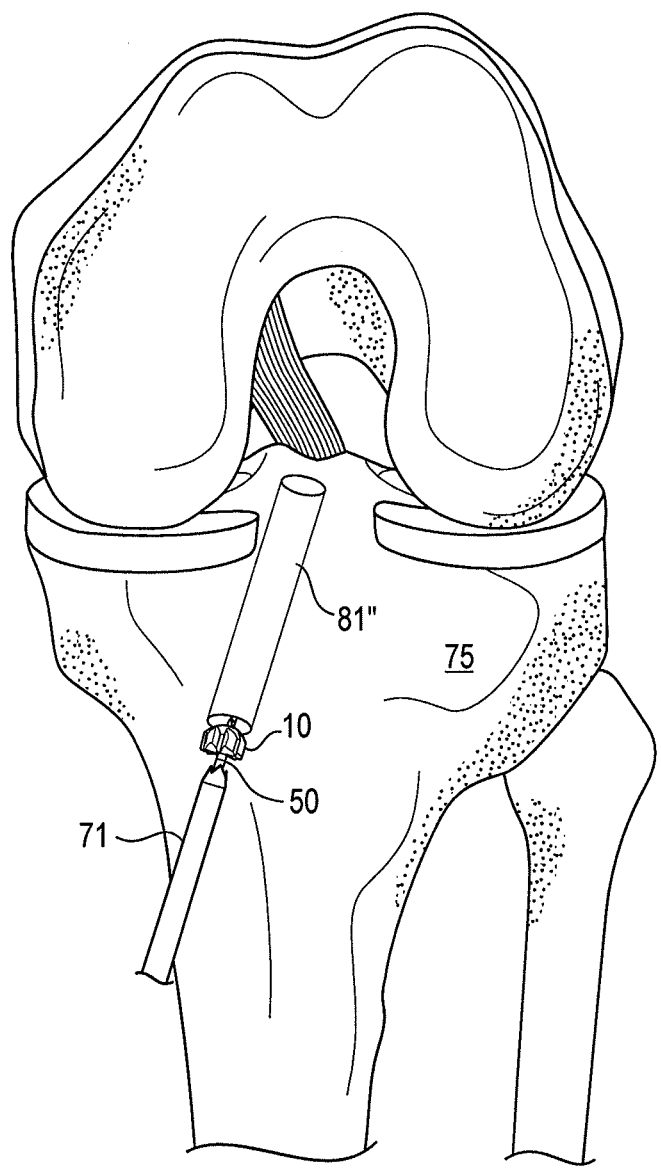

As is illustrated in FIGS. 8A-8B, the drill depth grommet 80 on the retrograde drill pin 50 is advanced to the end of the retrograde drill guide sleeve 71 for socket depth assessment during drilling. As shown in FIG. 9A, the retrograde drill pin 50 is retracted to facilitate retrograde drilling of the tibial joint surface and into the tibia 75 to create a tibial socket 81. A desired depth $D_1$, preferably 25 mm, is obtained by reading the markings 80" on the retrograde drill pin 50, recorded relative to the skin tibial surface prior to and during socket formation. Alternatively, a tibial tunnel 81" may be created by continuing drilling through the distal cortex, as shown in FIG. 9B.

Figure 10:
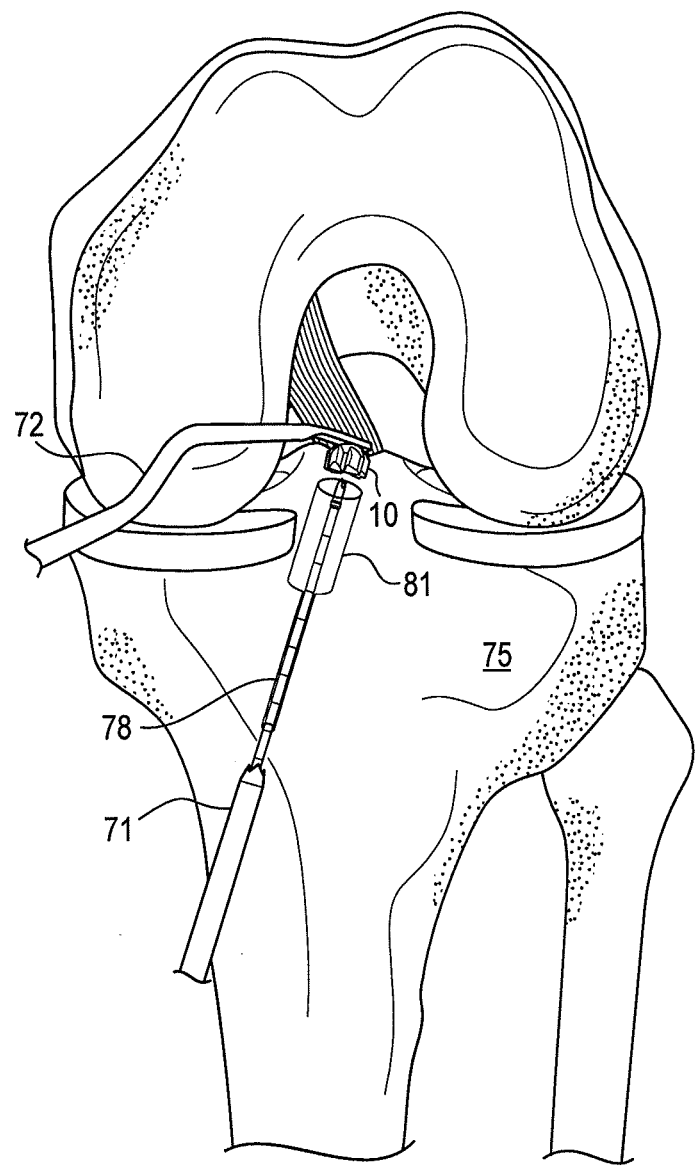
FIG. 10 schematically illustrates the formation of a tibial tunnel at a stage subsequent to that shown in FIG. 9A.
Figure 11:
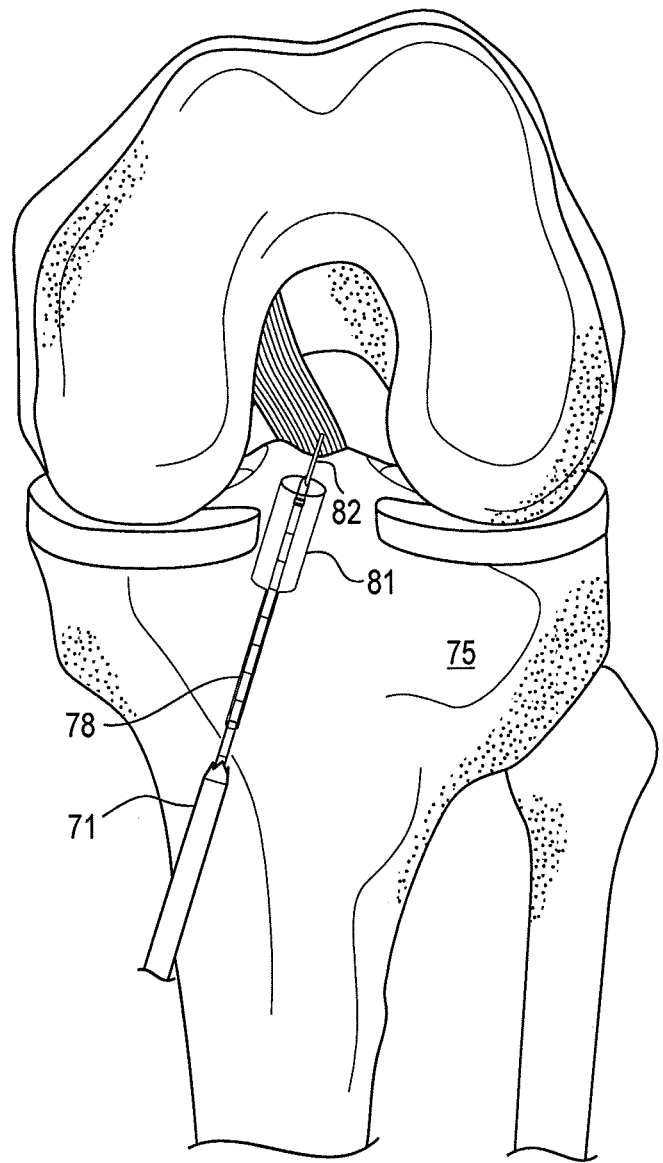
FIG. 11 schematically illustrates the formation of a tibial socket at a stage subsequent to that shown in FIG. 10 or FIG. 9B.

Once the desired socket depth $D_1$ is achieved, the retrograde drill pin 50 is advanced forward until the retrograde rotary cutter 10 engages the insertion post 74 on the tibial guide 72, as shown in FIG. 10. Reverse-drilling of the retrograde drill pin 50 securely engages the retrograde rotary cutter 10 on the insertion post 74 and simultaneously disengages the retrograde rotary cutter 10 from the threaded retrograde drill pin 50. The retrograde drill guide sleeve 71 is pulled back, the retrograde drill pin 50 is removed from C-ring 70, and the tibial guide 72 is removed from the knee joint. The retrograde drill pin 50 is left in place in the pin hole 78 and the tibial socket.

Figure 12:
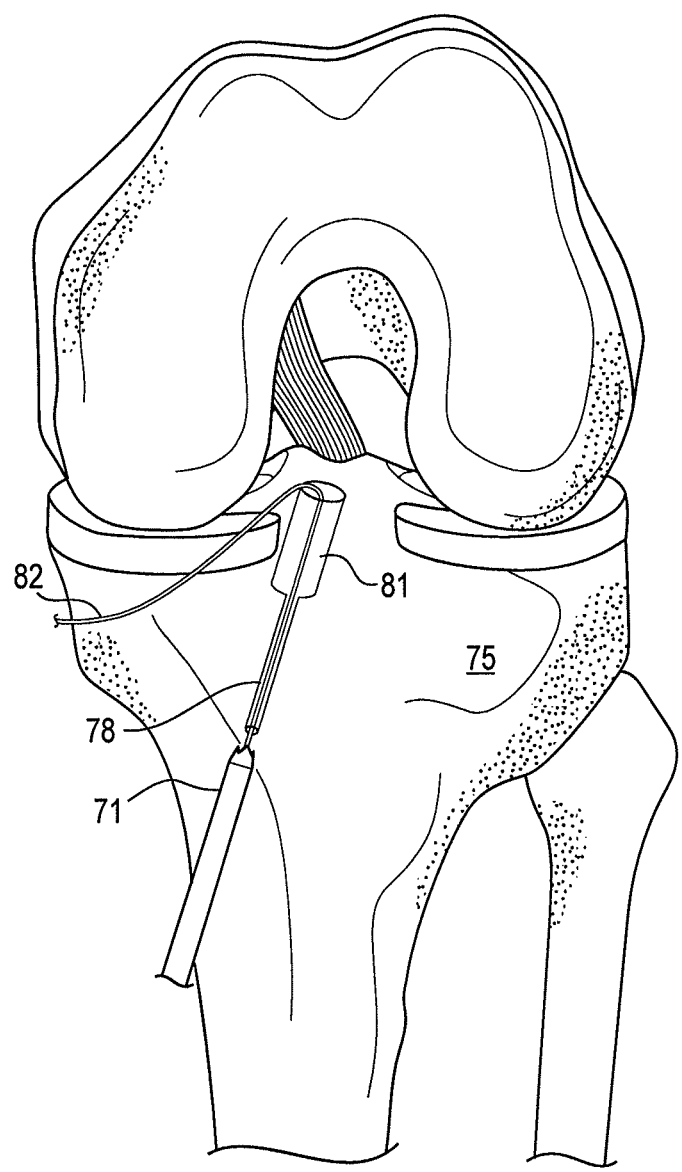
FIG. 12 schematically illustrates the formation of a tibial socket at a stage subsequent to that shown in FIG. 11.

Referring to FIG. 12, a tibial strand 82, such as Arthrex #2 FiberStick, described in U.S. Pat. No. 7,147,651, incorporated herein by reference, is passed through the cannulation of the retrograde drill pin 50 into the joint, and the retrograde drill pin 50 is withdrawn. The end of the tibial strand is retrieved from an anteromedial portal (not shown) and a loop is formed for subsequent use in the installation of a graft.

Creation of a femoral socket 84 continues in a manner similar to that for creating the tibial socket 81 and is described below with reference to FIGS. 13-18, which illustrate a schematic anterior view of a knee in which ACL reconstruction is performed according to the present invention. In the following embodiment of the present invention, a femoral socket 84 (shown completed in FIGS. 16-18) is formed in the femur 76.

Figure 13:
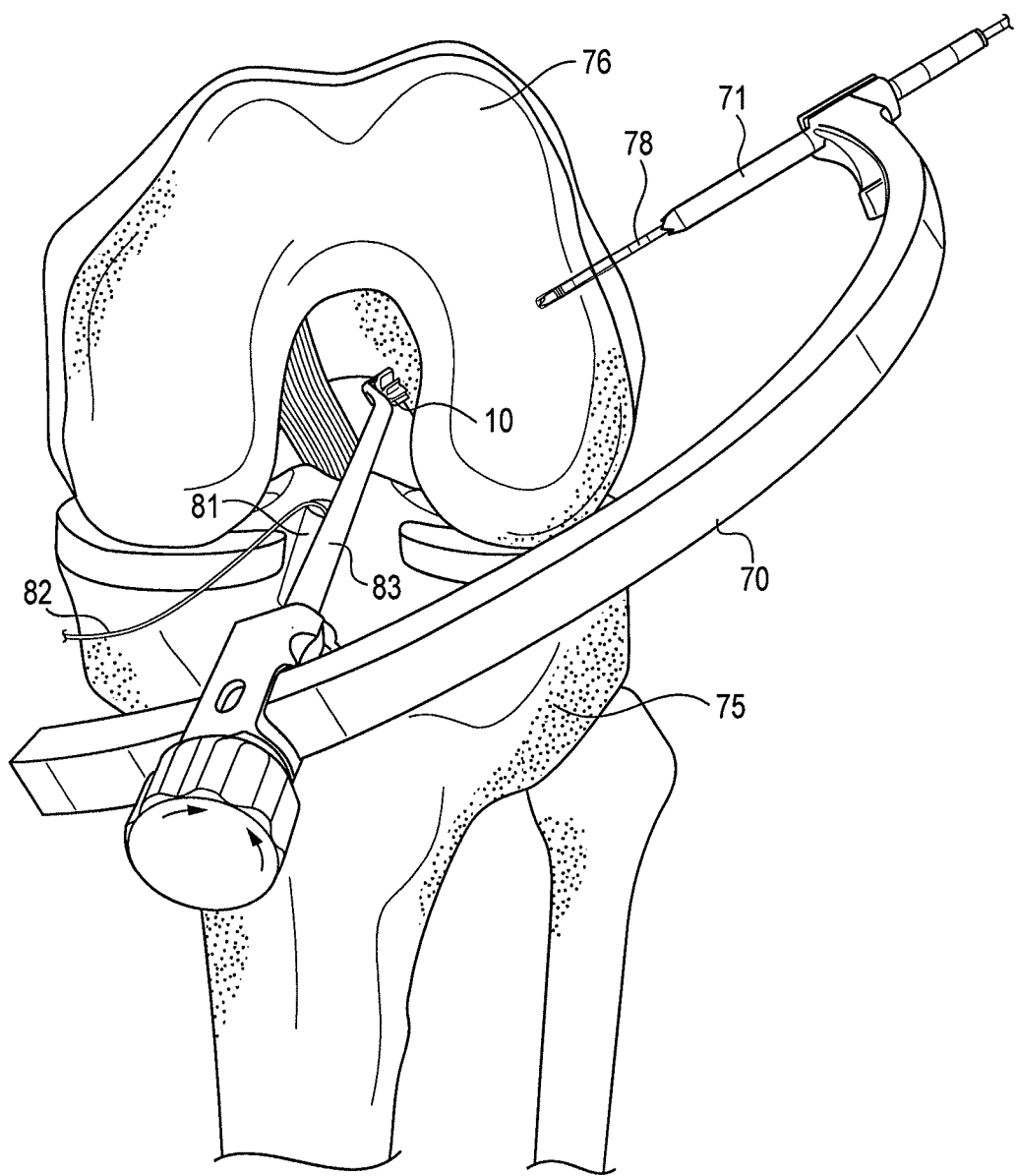
FIG. 13 schematically illustrates an initial stage in the formation of a femoral socket according to the present invention.
Figure 14:
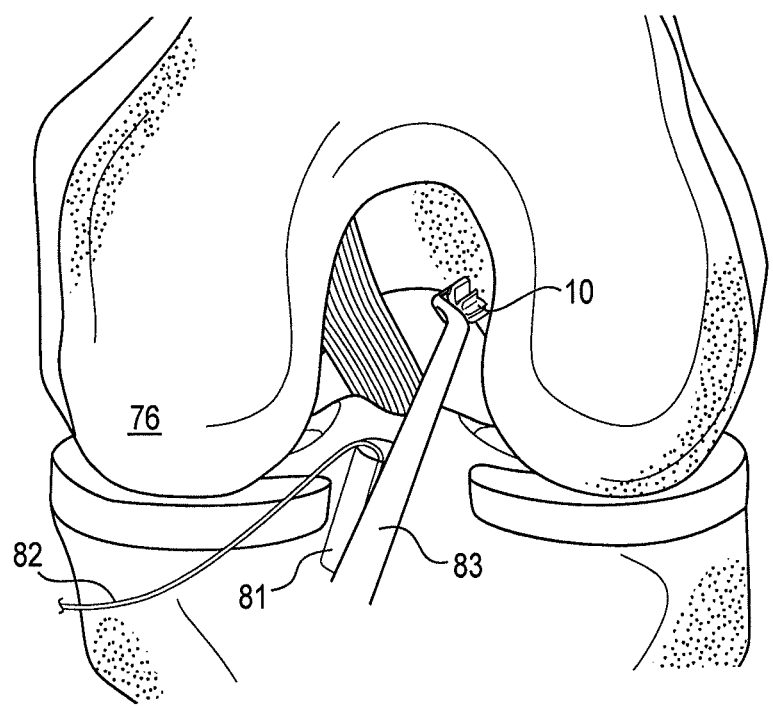
FIG. 14 schematically illustrates the formation of a femoral socket at a stage subsequent to that shown in FIG. 13.

Referring to FIGS. 13 and 14, the appropriate diameter retrograde rotary cutter 10 is threaded onto the insertion post 74 of the femoral guide 83. The femoral guide 83 is inserted through the anteromedial portal (not shown) and the retrograde rotary cutter 10 is placed on the anatomical origin of the ACL femoral origin. The retrograde drill pin 50 is adjusted to an appropriate angle, to avoid existing tunnels and fixation hardware, for insertion onto the femur 76. In pediatric cases, it is preferable to use a 90 degree guide to position the femoral socket inferior to the physis to avoid the growth plate.

Figure 15:
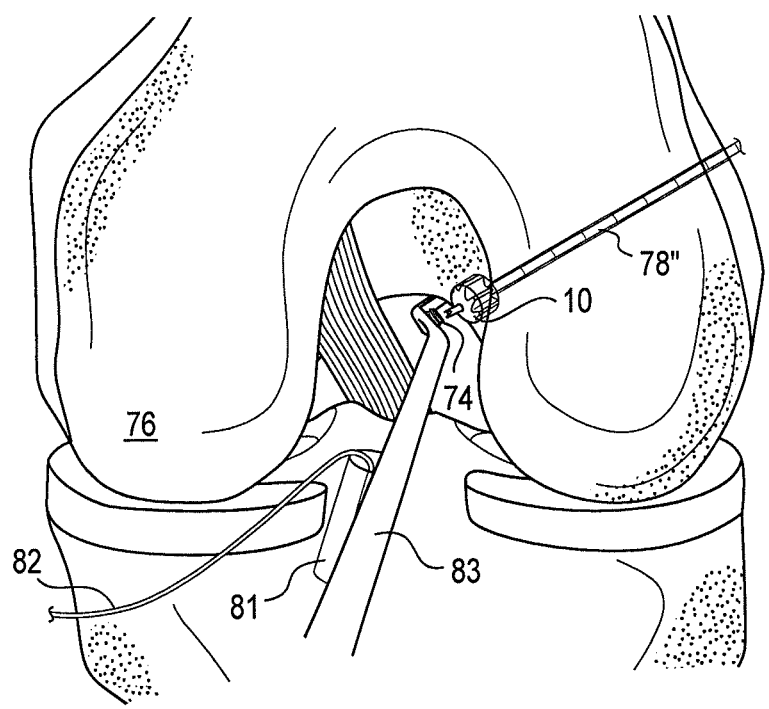
FIG. 15 schematically illustrates the formation of a femoral socket at a stage subsequent to that shown in FIG. 14.

Once the anatomical position in the joint for the femoral socket has been identified, and the appropriate drilling angle has been selected on C-ring 70, the retrograde drill guide sleeve 71 is inserted into the femur 76 through a small stab incision on the lateral thigh (not shown). The retrograde drill pin 50 is drilled through the femur 76, in a forward direction, to create pin hole 78" of a given diameter, for example 3 mm, as shown in FIG. 15.

Figure 16:
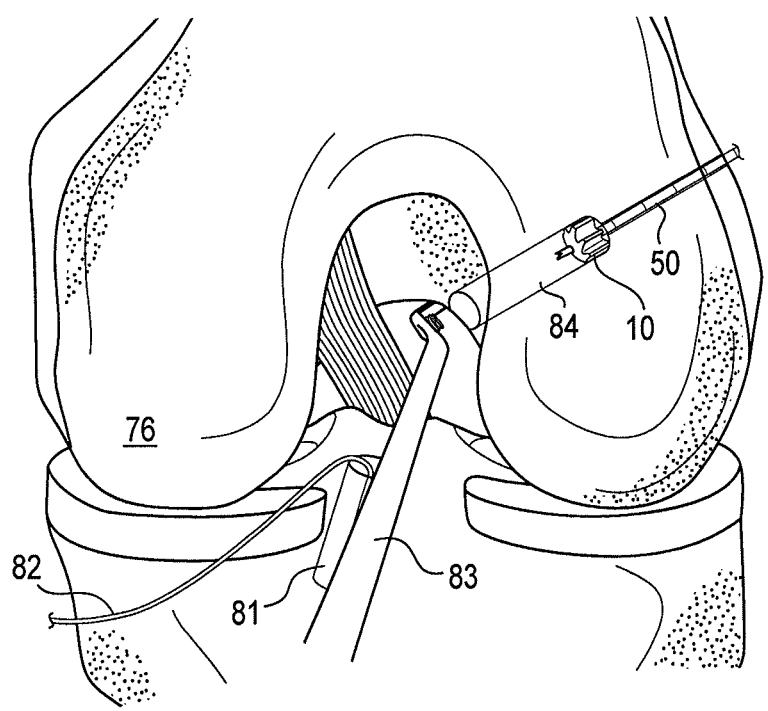
FIG. 16 schematically illustrates the formation of a femoral socket at a stage subsequent to that shown in FIG. 15.

The retrograde drill pin 50 is drilled through the femur 76 until contact is made with the retrograde rotary cutter 10 under arthroscopic control. Referring to FIG. 15, as threads of the retrograde drill pin 50 engage the retrograde rotary cutter 10, the reverse threads on the insertion post 74 of the femoral guide 83 facilitate simultaneous disengagement of the retrograde rotary cutter 10 from the insertion post 74 onto the retrograde drill pin 50. Once securely engaged within the retrograde rotary cutter 10, the retrograde drill pin 50 is rotated with a power driver (not shown) and retracted (retrograde) to cut through the femoral joint surface and into the femur 76 to create a femoral socket 84, as shown in FIGS. 15-16. A desired depth $D_2$, preferably 25 mm, is obtained by reading the markings 80" on the retrograde drill pin 50, recorded relative to the skin femoral surface prior to and during socket formation.

Figure 17:
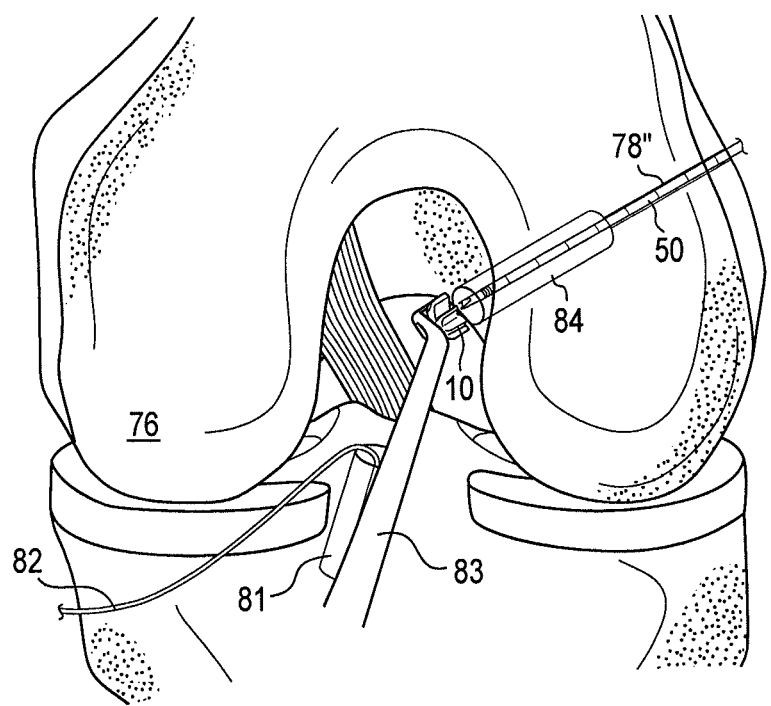
FIG. 17 schematically illustrates the formation of a femoral socket at a stage subsequent to that shown in FIG. 16.

Once the desired socket depth $D_2$ is achieved, the retrograde drill pin 50 is advanced forward until the retrograde rotary cutter 10 engages the insertion post 74 on the femoral guide 83, as shown in FIG. 17. Reverse-drilling of the retrograde drill pin 50 securely engages the retrograde rotary cutter 10 on the insertion post 74 and simultaneously disengages the retrograde rotary cutter 10 from the threaded retrograde drill pin 50. The retrograde drill guide sleeve 71 is pulled back, the retrograde drill pin 50 is removed from C-ring 70, and the femoral guide 83 is removed from the knee joint. The retrograde drill pin 50 is left in place in the pin hole 78" and the femoral socket 84.

Figure 18:
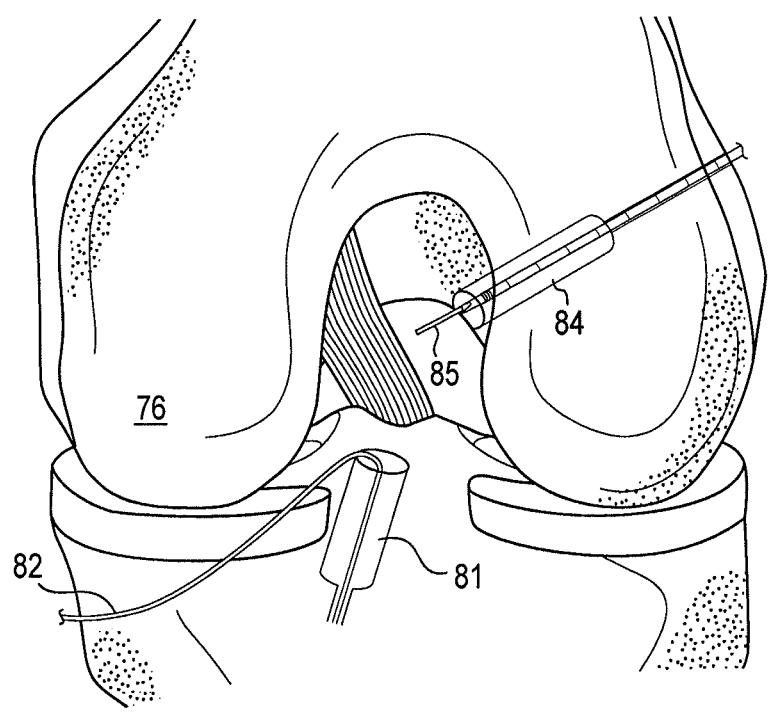
FIG. 18 schematically illustrates the formation of a femoral socket at a stage subsequent to that shown in FIG. 17.

Referring to FIG. 18, a femoral strand 85, such as Arthrex #2 FiberStick, described in U.S. Patent Application Publ. No. 2003/0153948, is passed through the cannulation of the retrograde drill pin 50 into the joint and the retrograde drill pin 50 is withdrawn. The end of the femoral strand 85 is retrieved from an anteromedial portal (not shown) and a loop 91 is formed for subsequent use in the installation of a graft.

A soft tissue graft or a composite femoral bone/tendon allograft is prepared for insertion and fixation into the femoral socket 84 and tibial socket 81. The graft is selected so that its diameter corresponds to the diameters of the femoral and tibial sockets 84, 81. Alternatively, the correct diameter of the retrograde rotary cutter 10 may be selected to correspond to the diameter of a previously-prepared graft. The graft 86 is slightly shorter than the summed lengths of the femoral and tibial sockets and the intraarticular length of a damaged ligament origin and insertion points, to facilitate appropriate tension in the graft 86 during fixation. For example, assuming that the length $D_1$ of the tibial socket 81 is about 25 millimeters, the length $D_2$ of the femoral socket 84 is about 25 millimeters, and the intraarticular length D between the two sockets is about 30 millimeters, the total length L of the graft 86 is slightly less than about (25+25+30) millimeters.

Figure 19:
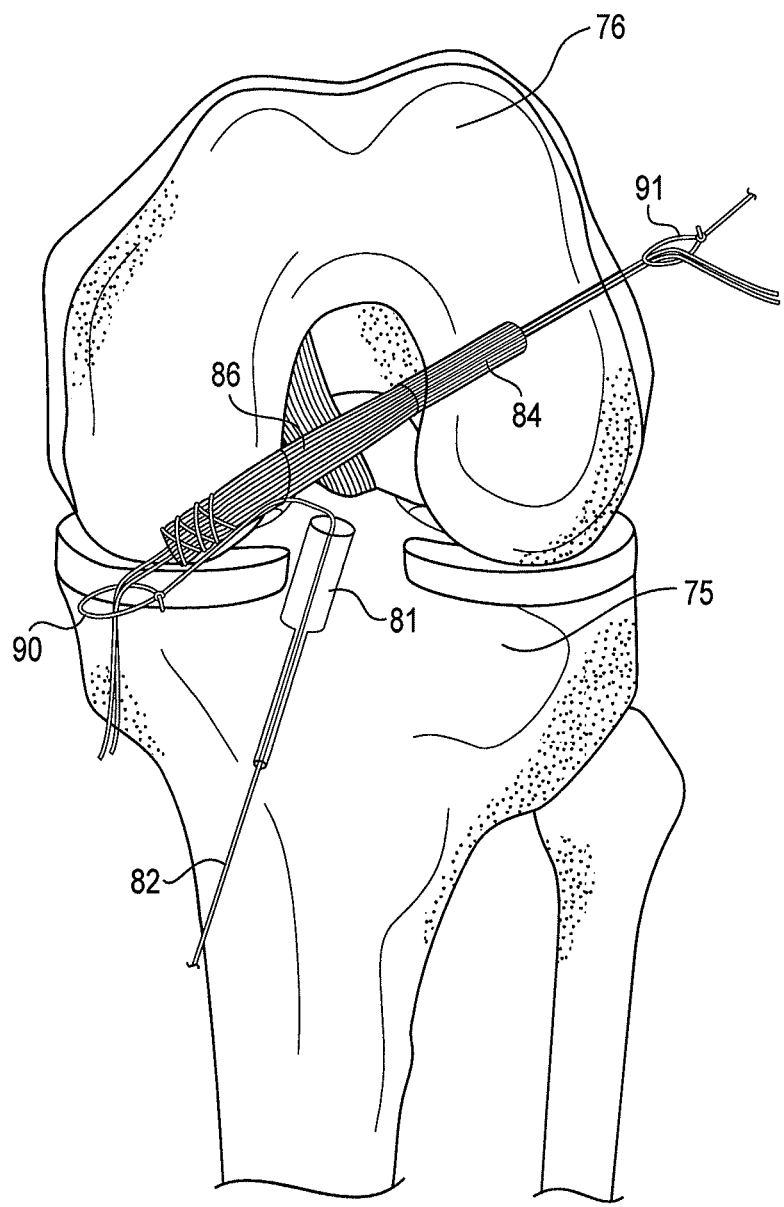
FIG. 19 illustrates a schematic view of a knee joint undergoing graft insertion according to an embodiment of the present invention.
Figure 20:
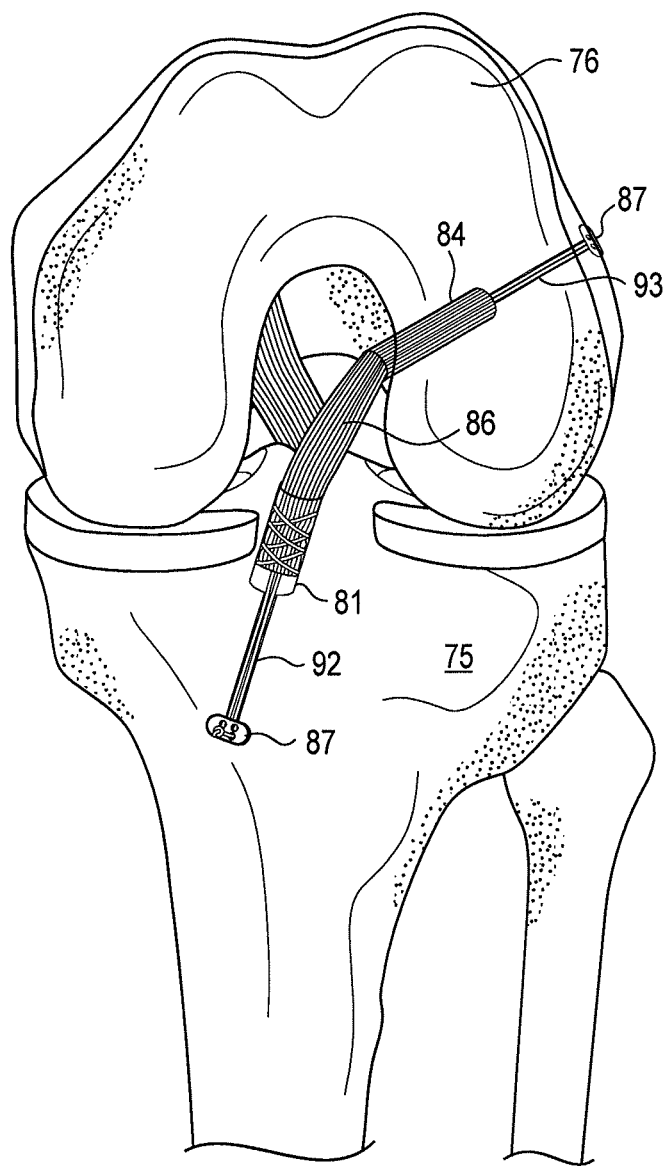
FIG. 20 illustrates a schematic view of a knee joint having undergone graft insertion and fixation according to an embodiment of the present invention.

Installation of the graft 86 is illustrated schematically in FIGS. 19-20. The graft 86 is pulled through the anteromedial portal (not shown) by the loops 90, 91 formed in the tibial strand 82 and the femoral strand 85. The ends of the graft 86 are drawn into the femoral 84 and tibial 81 sockets, as shown in FIGS. 19-20. The graft suture 93 is tied over the lateral femoral cortex. The knee is brought into near extension, the graft 86 appropriately tensioned and the graft suture 92 is tied over the tibial cortex. A graft tension measuring device, such as Arthrex Tensioning Device AR-4002, may be used to quantify the tension in the graft 86 during tibial fixation. The sutures 92, 93 may be tied over a button 87, such as the Arthrex titanium Suture Button, Part No. AR-8920. The sutures 92, 93 may be secured in any conventional manner, such as using ligament washers and post designs, or interference screws placed in a retrograde fashion with a specially designed retrograde screw driver, or with a cross pin.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description, but instead is limited by the scope of the appended claims.

What is claimed is:

1. A system for retrograde drilling of openings in bone, comprising:
    a rotary cutter comprising a cylindrically shaped body provided with a cannulation and radially outward cutting teeth for retrograde drilling of a hole in bone;
    a drill guide including a post for engaging and mounting the rotary cutter;
    a pin having a distal end corresponding to the cannulation of the rotary cutter, for engaging the rotary cutter, wherein the rotary cutter is transferred from the drill guide to the pin by advancing the pin into the cannulation of the rotary cutter and rotating the pin in a first direction to engage the pin with the rotary cutter mounted on the drill guide, and simultaneously disengage the rotary cutter from the drill guide; and
    a C-ring for mounting the drill guide and positioning the drill guide with respect to the bone, the C-ring further including a sleeve for guiding the pin such that the pin is directed into engagement with the cannulation of the rotary cutter mounted on the drill guide, as the pin is advanced through the sleeve.

2. The system of claim 1, wherein the position of the drill guide is adjustable on the C-ring to facilitate angular adjustment of the drill guide relative to the pin.

3. The system of claim 2, wherein the C-ring is provided with calibrated angular scale markings.

4. The system of claim 2, wherein the pin comprises a cannulated shaft having a proximal end and a distal end, a fluted region formed on the distal end of the cannulated shaft for drilling through bone; and a threaded portion located near the distal end of the cannulated shaft and corresponding to inner threads of the cannulation of a rotary cutter.

5. The system of claim 4, wherein the pin is provided with a depth-measuring grommet located axially on the retrograde pin for depth assessment during drilling.

* * * * *